United States Patent [19]

Broger et al.

[11] Patent Number: 4,620,013

[45] Date of Patent: Oct. 28, 1986

[54] CHIRAL PHOSPHINES

[75] Inventors: Emil A. Broger, Magden; Yvo Crameri, Oberwil, both of Switzerland

[73] Assignee: Hoffmann-La Roche Inc., Nutley, N.J.

[21] Appl. No.: 744,584

[22] Filed: Jun. 14, 1985

Related U.S. Application Data

[62] Division of Ser. No. 458,418, Jan. 17, 1983, Pat. No. 4,539,411.

[30] Foreign Application Priority Data

Feb. 5, 1982 [CH] Switzerland ............................ 711/82
Dec. 8, 1982 [CH] Switzerland .......................... 7010/82

[51] Int. Cl.$^4$ .......................... C07F 9/65; C07F 15/00
[52] U.S. Cl. .................................................... 548/412
[58] Field of Search ........................................ 548/412

[56] References Cited

U.S. PATENT DOCUMENTS

| | | | |
|---|---|---|---|
| 4,119,652 | 10/1978 | Knowles .......................... | 548/412 X |
| 4,168,381 | 9/1979 | Fischer, Jr. et al. ................ | 548/320 |
| 4,343,741 | 8/1982 | Townsend et al. .................. | 548/412 |
| 4,424,312 | 1/1984 | Stille ..................................... | 525/274 |

FOREIGN PATENT DOCUMENTS

| | | | |
|---|---|---|---|
| 0160365 | 12/1979 | Japan .................................. | 548/412 |
| 0145891 | 9/1982 | Japan .................................. | 548/412 |
| 1592536 | 7/1981 | United Kingdom . | |
| 2097003A | 10/1982 | United Kingdom . | |

OTHER PUBLICATIONS

Knowles et al., Catalytic Aspects of Metal Phosphine Complexes, 1982, pp. 325–336, Adv. Chem. Series, 1982.
Knowles et al., Chem. Abst., vol. 97, 71596n, (1982).
Broger et al., Chem. Abst., vol. 100, 22797a, (1984).
Achiwa, K., J.A.C.S., vol. 98, No. 25, pp. 8265–8266 (1976).
Achiwa, K., Tetrahedron Letters, No. 50, 4431-2 (1977).
Achiwa, K., Chemistry Letters, 297–298 (1978).
Knowles, W. et al., "Fundamental Research in Homogeneous Catalysis", Vol. III, pp. 537–548, especially pp. 541 and 542.
Achiwa, J. Organometallic Chemistry, 218 (1981) 249–260.
Ojima et al., J.C.S. Chem. Comm. (1977) 428–430.
Ojima et al., J. Org. Chem. 43, No. 18, 3444-6 (1978).
Patents Abstracts of Japan, C-60, 5, No. 9, Jun. 25, 1981.
Brunner, Chemie in Unserev Zeit, 14, No. 6, (1980), 177–183.

*Primary Examiner*—Donald G. Daus
*Assistant Examiner*—Diana G. Rivers
*Attorney, Agent, or Firm*—Jon S. Saxe; Bernard S. Leon; George W. Johnston

[57] ABSTRACT

Novel chiral phosphines are disclosed which when complexed with rhodium provide catalyst compositions for asymmetric hydrogenations.

8 Claims, No Drawings

CHIRAL PHOSPHINES

This is a divisional of application Ser. No. 458,418, filed Jan. 17, 1983, now U.S. Pat. No. 4,539,411.

BACKGROUND OF THE INVENTION

Achiwa in J.A.C.S., 98, 8265 (1976) describes BPPM [(2S,4S)-N-butoxycarbonyl-4-diphenyl-phosphino-2-diphenylphosphinomethyl-pyrrolidine] and the use of this compound in the form of a rhodium complex as a catalyst for asymmetric hydrogenation.

Achiwa in papers in Tetrahedron Letters, No. 50, 4431 (1977) and Chemistry Letters, 297-998 (1978) has described the asymmetric hydrogenation of ketopantolactons with a rhodium complex of BPPM.

Finally, Knowles et al. in "Fundamental Research in Homogeneous Catalysis", Vol. III, pages 537-548, particularly page 542, Editor: Tsutsui Publisher, Plenum Press, New York, refers erroneously to phosphines corresponding to formula I herein where $R^1$ is $-SO_2-CH_3$. However, from the content of the text it is clear that the pivaloyl group was intended.

DESCRIPTION OF THE INVENTION

The present invention is concerned with novel chiral phosphines of the general formula

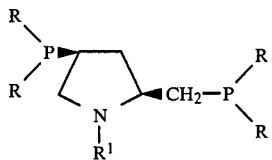

I wherein R represents aryl and $R^1$ represents a group of the formula

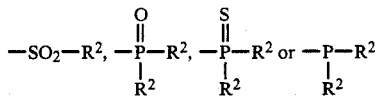

in which $R^2$ represents aryl, diarylamino, di(lower alkyl)amino, hydroxy, aryloxy or lower alkoxy.

The invention is also concerned with the manufacture of the phosphines of formula I and their use for asymmetric hydrogenations.

The term "aryl" signifies in the scope of the present invention phenyl which optionally carries in the para- and/or meta-position lower alkyl or lower alkoxy groups, preferably methyl or methoxy groups, or di(-lower alkyl)amino groups, preferably dimethylamino groups. Moreover, two aryl groups attached to the same phosphorus atom can be bonded together directly via the o-position or via a methylene, ethylene or propylene group. The term "aryloxy" signifies groups in which the aryl moiety has the foregoing significance. The term "lower alkyl" signifies in the scope of the present invention straight-chain and branched-chain alkyl groups containing 1 to 7 carbon atoms such as, for example, methyl, ethyl, propyl, isopropyl, n-butyl, isobutyl, tert.butyl and the like. The term "lower alkoxy" signifies groups in which the alkyl moiety has the foregoing significance. Furthermore, the notation "◄" signifies that the corresponding group is situated above the plane of the molecule, while the notation " ⦀⦀⦀ " signifies that the corresponding group is situated below the plane of the molecule.

Preferred phosphines of formula I are those in which R represents phenyl, p-tolyl, m-tolyl or 3,5-xylyl and $R^2$ in the groups $R^1$ represents phenyl, p-tolyl, m-tolyl, phenoxy or di(lower alkyl)amino. Especially preferred phosphines are, moreover, those in which $R^1$ represents the group

The following are examples of preferred compounds of formula I:

(2S,4S(-4-(Diphenylphosphino)-2-[(diphenylphosphino)methyl]-1-(diphenylphosphinyl)-pyrrolidine;
(2S,4S)-4-(di-p-tolylphosphino)-2-[(di-p-tolylphosphino)methyl]-1-(diphenylphosphinyl)-pyrrolidine;
(2S,4S)-4-(di-m-tolylphosphino)-2-[(di-m-tolylphosphino)methyl]-1-(diphenylphosphinyl)pyrrolidine;
(2S,4S)-4-(di-3,5-xylylphosphino)-2-[(di-3,5-xylylphosphino)methyl]-1-(diphenylphosphinyl)-pyrrolidine;
(2S,4S)-4-(diphenylphosphino)-2-[(diphenylphosphino)methyl]-1-[di-p-tolylphosphinyl]-pyrrolidine;
(2S,4S)-4-(diphenylphosphino)-2-[(diphenylphosphino)methyl]-1-(di-m-tolylphosphinyl)-pyrrolidine;
diphenyl[(2S,4S)-4-(diphenylphosphino)-2-[(diphenylphosphino)methyl]-1-pyrrolidinyl]-phosphonate;
diphenyl[(2S,4S)-4-(di-p-tolylphosphino)-2-[(di-p-tolylphosphino)methyl]-1-pyrrolidinyl]-phosphonate;
diphenyl[(2S,4S)-4-(di-m-tolylphosphino)-2-[(di-m-tolylphosphino)methyl]-1-pyrrolidinyl]-phosphonate;
[(2S,4S)-4-(diphenylphosphino)-2-[(diphenylphosphino)methyl]-1-pyrrolidinyl]-N,N,N',N'-tetramethylphosphonic acid diamide;
[(2S,4S)-4-(di-p-tolylphosphino)-2-[(di-p-tolylphosphino)methyl]-1-pyrrolidinyl]-N,N,N',N'-tetramethylphosphonic acid diamide;
[(2S,4S)-4-(di-m-tolylphosphino)-2-[(di-m-tolylphosphino)methyl]-1-pyrrolidinyl]-N,N,N',N'-tetramethylphosphonic acid diamide;
[(2S,4S)-4-(diphenylphosphino)-2-[(diphenylphosphino)methyl]-1-pyrrolidinyl]-diphenylphosphine;
(2S,4S)-4-(diphenylphosphino)-2-[(diphenylphosphino)methyl]-1-(p-tolylsulphonyl)-pyrrolidine;
(2S,4S)-4-(di-p-tolylphosphino)-2-[(di-p-tolylphosphino)methyl]-1-(p-tolylsulphonyl)-pyrrolidine;
2S,4S)-4-(di-m-tolylphosphino)-2-[(di-m-tolylphosphino)methyl]-1-(p-tolylsulphonyl)-pyrrolidine;
phenyl(2S,4S)-4-(diphenylphosphino)-2-[(diphenylphosphino)methyl]-1-pyrrolidinesulphonate;
phenyl(2S,4S)-4-(di-p-tolylphosphino)-2-[(di-p-tolylphosphino)methyl]-1-pyrrolidinesulphonate;
phenyl(2S,4S)-4-(di-m-tolylphosphino)-2-[(di-m-tolylphosphino)methyl]-1-pyrrolidinesulphonate;
(2S,4S)-4-diphenylphosphino)-2-[(diphenylphosphino)methyl]-N,N-dimethyl-1-pyrrolidinesulphonamide;
(2S,4S)-4-(di-p-tolylphosphino)-2-[(di-p-tolylphosphino)methyl]-N,N-dimethyl-1-pyrrolidinesulphonamide;
(2S,4S)-4-(di-m-tolylphosphino)-2-[(di-m-tolylphosphino)methyl]-N,N-dimethyl-1-pyrrolidinesulphonamide;
(2S,4S)-4-(diphenylphosphino)-2-[(diphenylphosphino)methyl]-1-pyrrolidinesulphonic acid;

[(2S,4S)-2-(5H-dibenzophosphol-5-ylmethyl)-4-(5H-dibenzophosphol-5-yl)-1-pyrrolidinyl]diphenylphosphine oxide;

5-[(2S,4S)-2-[(diphenylphosphino)methyl]-4-(diphenylphosphino)-1-pyrrolidinyl]-5H-dibenzophosphol 5-oxide;

[(2S,4S)-2-[5(10H)-acridophosphinylmethyl]-4-(5(10H)-acridophosphinyl]-1-pyrrolidinyl]diphenylphosphine oxide;

5[(2S,4S)-2-[(diphenylsphosphino)methyl]-4-(diphenylphosphino)-1-pyrrolidinyl]-5,10-dihydroacridophosphine 5-oxide;

5-[(2S,4S)-2-(5H-dibenzophosphol-5-ylmethyl)-4-(5H-dibenzophosphol-5-yl)-1-pyrrolidinyl]-5H-dibenzophosphol 5 oxide; and

[(2S,4S)-2-[(diphenylphosphino)methyl]-4-(diphenylphosphino)-1-pyrrolidinyl]diphenylphosphine sulphide.

The compounds of formula I provided by the invention can be manufactured by (a) reacting a compound of the general formula

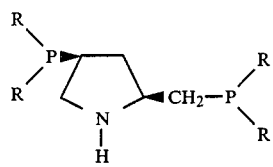

II wherein R has the significance given earlier, with a compound of the general formula R$^3$—SO$_2$—R$^2$,  IIIa (R$^2$—SO$_2$)$_2$O,  IIIb

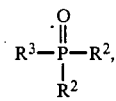 IIIc

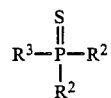 IIId or

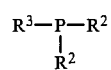 IIIe wherein R$^2$ has the significance given earlier and R$^3$ represents chlorine or fluorine, or (b) reacting a compound of the general formula

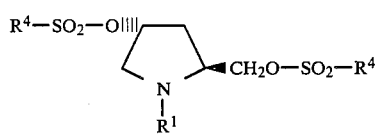 IV wherein R$^1$ has the significance given earlier and R$^4$ represents aryl or lower alkyl, with a compound of the general formula

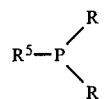 V wherein R has the significance given earlier and R$^5$ represents lithium, sodium, potassium or magnesium halide.

The reaction of the compounds of formula II with the compounds of formulae IIIa–IIIe can be carried out in a manner known per se, whereby it must be carried out with the strict exclusion of oxygen, namely under an inert gas atmosphere (e.g. under nitrogen, argon and the like). The reaction can conveniently be carried out in an inert organic solvent such as an aromatic hydrocarbon (e.g. benzene, toluene and the like) or an ether (e.g. diethyl ether, tetrahydrofuran, dioxan and the like) and, if necessary, with the addition of a tertiary amine. The temperature and the pressure at which this reaction is carried out are not critical and accordingly the reaction can be carried out readily at about room temperature and atmospheric pressure.

The compounds of formulae II and IIIa–IIIe used as starting materials are known compounds or analogues of known compounds which can be prepared readily in an analogous manner to the preparation of the known compounds.

The reaction of the compounds of formula IV with the compounds of formula V can be carried out in a manner known per se, whereby it must be carried out with the strict exclusion of oxygen, namely under an inert gas atmosphere (e.g. under nitrogen, argon and the like). The reaction is conveniently carried out in an inert organic solvent such as an ether (e.g. tetrahydrofuran, dioxan, diethyl ether and the like), if desired in the presence of a hydrocarbon (e.g. hexane, benzene, toluene and the like). The reaction is conveniently carried out at a temperature of about −15° C. to about room temperature, preferably at about −10° C. to about 0° C. The pressure at which the reaction is carried out is not critical and accordingly the reaction can be carried out readily at atmospheric pressure.

The compounds of formula IV used as starting materials are novel compounds and are likewise an object of the present invention. They can, however, be prepared in a manner known per se; for example, in accordance with Reaction Schemes I and II hereinafter. In these Reaction Schemes Ts signifies the tosyl group and A signifies the group

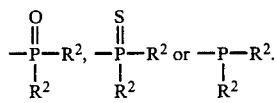

Reaction Scheme I

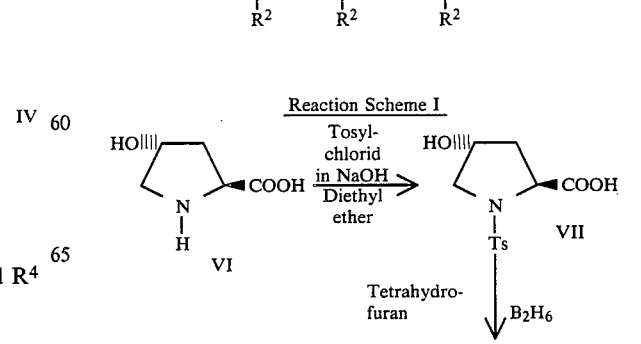

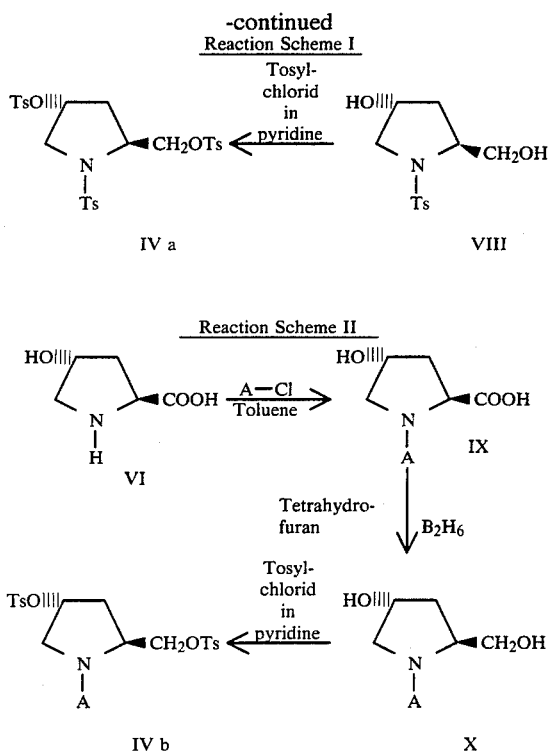

The compounds of formula V used as starting materials are known or are analogues of known compounds which can be prepared readily in a manner analogous to the preparation of the known compounds.

The phosphines of formula I provided by the invention form complexes with rhodium which can be used as catalysts in asymmetric hydrogenations. These catalysts, i.e. the complexes of rhodium and the phosphines of formula I, are novel and are also an object of the present invention. These catalysts can be manufactured in a manner which is simple and known per se; for example, by reacting a compound of formula I with a compound yielding rhodium in a suitable inert organic solvent. Suitable compounds yielding rhodium are, for example, rhodium trichloride hydrate, rhodium tribromide hydrate, rhodium sulphate or organic rhodium complexes with ethylene, propylene and the like as well as with bis-olefins such as 1,5-cyclooctadiene, 1,5-hexadiene, bicyclo-2,2,1-hepta-2,5-diene or with other dienes which form readily soluble complexes with rhodium. Preferred compounds yielding rhodium are u,u′-dichloro-bis-[bis-(olefin)-rhodium (I)], for example u,u′-dichloro-bis-(1,5-cyclooctadiene-rhodium (I)] or u,u′-dichloro-bis-[(norbornadiene)-rhodium (I)].

As mentioned earlier, the phosphines provided by the invention serve as ligands in rhodium complexes which are used as catalysts in asymmetric hydrogenations. They are especially interesting in connection with the asymmetric hydrogenation of α-keto-carboxylic acid esters to the corresponding α-hydroxy-carboxylic acid esters and especially of dihydro-4,4-dimethyl-2,3-furandione(ketopantolactone) to the corresponding R-(α-hydroxy-β,β-dimethyl-γ-butyrolactone)[R-(−)-pantolactone].

In carrying out the aforementioned asymmetric hydrogenations, the phosphines of formula I can be brought into contact as such, in a solution of an asymmetric compound to be hydrogenated, with a compound yielding rhodium. On the other hand, the phosphines of formula I can be reacted firstly in a suitable solvent with a compound yielding rhodium to give the corresponding catalyst complex and this can then be added to a solution of an asymmetric compound to be hydrogenated.

Not only the reaction of the phosphines of formula I with the compound yielding rhodium but also the aforementioned asymmetric hydrogenations can be carried out in suitable organic solvents which are inert under the reaction conditions. Especially suitable organic solvents are lower alkanols such as, for example, methanol or ethanol, aromatic hydrocarbons such as benzene or toluene, cyclic ethers such as tetrahydrofuran or dioxan, esters such as, for example, ethyl acetate or mixtures thereof and the like. The ratio between rhodium and the ligands of formula I conveniently lies between about 0.05 and about 5 mol, preferably between about 0.5 and about 2 mol, of rhodium per mol of ligand of formula I. The ratio between rhodium in the complexes with the ligands of formula I and the compounds to be hydrogenated conveniently lies between about 0.00001 and about 5 wt.%, preferably between about 0.001 and about 0.5 wt.%.

The asymmetric hydrogenations using rhodium complexes with the ligands of formula I can conveniently be carried out at temperatures of about 20° C. to about 100° C., preferably from about 40° C. to about 90° C. These hydrogenations are conveniently carried out under pressure, especially under a pressure of about 1 to 100 bar, preferably 2 to 50 bar.

The following Examples illustrate the present invention:

EXAMPLE 1

1.01 g (2.23 mmol) of (2S,4S)-4-diphenylphosphino-2-diphenylphosphinomethylpyrrolidine, 1.46 ml (13.38 mmol) of N-methylmorpholine and 30 ml of toluene were placed in a 500 ml sulphonation flask which was provided with a stirrer, thermometer, dropping funnel and argon gasification. While stirring there was then added dropwise thereto at room temperature within 10 minutes a solution of 0.79 g (3.35 mmol) of diphenylphosphinyl chloride in 10 ml of toluene. The reaction was finished after 7 hours. The mixture was then filtered through a sintered glass suction filter and the filtrate was evaporated on a rotary evaporator at 60° C./17 mbar. The residue (2.2 g) was taken up in 30 ml of diethyl ether and treated with 30 ml of 3N hydrochloric acid. The ether phase was then separated and the aqueous phase was extracted a further twice with 30 ml of diethyl ether each time. The extracts were dried over sodium sulphate, filtered off and concentrated on a rotary evaporator at 60° C./17 mbar. For purification the residue (1.57 g) was chromatographed over 140 g of Kieselgel 60 (0.063 to 0.20 mm granular size). A mixture of benzene/ethyl acetate/ethanol (8:2:1) was used as the eluant. After evaporation of the solvent and drying for 16 hours/1 mbar, there was obtained 1.12 g (76.8%) of pure (2S,4S)-4-(diphenylphosphino)-2-[(diphenylphosphino)methyl]-1-(diphenylphosphinyl)-pyrrolidine.

Melting point: sintering from 65° C., clear melting at 130° C. $[\alpha]_D^{20} = -21.4°$ (c=0.5 in benzene).

The following compounds are manufactured in an analogous manner:

(2S,4S)-4-(Di-p-tolylphosphino)-2-[(di-p-tolylphosphino)methyl]-1-(diphenylphosphinyl)-pyrrolidine, $[\alpha]_D^{20} = -33.2°$ (c=0.5 in benzene);

(2S,4S)-4-(di-m-tolylphosphino)-2-[(di-m-tolylphosphino)methyl]-1-(diphenylphosphinyl)-pyrrolidine, $[\alpha]_D^{20} = -25.8°$ (c=0.6 in benzene);

(2S,4S)-4-(diphenylphosphino)-2-[(diphenylphosphino)methyl]-1-(di-p-tolylphosphinyl)-pyrrolidine, $[\alpha]_D^{20} = -13.8°$ (c=0.5 in benzene);

(2S,4S)-4-(diphenylphosphino)-2-[(diphenylphosphino)methyl]-1-(di-m-tolylphosphinyl)-pyrrolidine, $[\alpha]_D^{20} = -21.3°$ (c=0.6 in benzene);

[(2S,4S)-4-(diphenylphosphino)-2-[(diphenylphosphino)methyl]-1-pyrrolidinyl]-diphenylphosphine, $[\alpha]_D^{20} = -64.0°$ (c=0.6 in benzene);

diphenyl[(2S,4S)-4-(diphenylphosphino)-2-[(diphenylphosphino)methyl]-1-pyrrolidinyl]-phosphonate, $[\alpha]_D^{20} = -63.3°$ (c=0.6 in benzene); and

[(2S,4S)-4-(diphenylphosphino)-2-[(diphenylphosphino)methyl]-1-pyrrolidinyl]-N,N,N',N'-tetramethylphosphonic acid diamide, $[\alpha]_D^{20} = -60.7°$ (c=0.6 in benzene).

EXAMPLE 2

7.5 g (38 mmol) of diphenylphosphine were dissolved in 25 ml of tetrahydrofuran in a 200 ml sulphonation flask, provided with a stirrer, thermometer, two dropping funnels, argon gasification and cooling bath, and the solution was cooled to 0° C. Thereupon, 28 ml of a 1.5M n-butyl lithium solution (hexane; 42 mmol) were added dropwise within 15 minutes at 0°–5° C. while stirring, the initially colourless solution becoming intensively orange-red in colour. A solution of 9.7 g (16.7 mmol) of (2S,4R)-1-(p-tolylsulphonyl)-4-[(p-tolylsulphonyl)oxy]-2-pyrrolidinylmethyl p-toluenesulphonate in 50 ml of tetrahydrofuran was then added dropwise at −5° C. within 30 minutes, the solution becoming pale orange in colour. After a reaction time of 5 hours at 0° C., a few drops of water were added and the solution was then evaporated on a rotary evaporator at 60° C./17 mbar. The residue was dissolved in 100 ml of benzene, washed three times with 100 ml of water each time and the aqueous phases were back-washed with 100 ml of benzene. The combined benzene extracts were evaporated on a rotary evaporator at 60° C./17 mbar. The product obtained (15.2 g of yellowish oil), which crystallizes partially upon standing, was, for purification, dissolved in benzene and the solution was filtered over 240 g of Kieselgel 60 (0.63–0.20 mm granular size). After evaporation of the solvent and drying for 16 hours at 40° C./17 mbar, there were obtained 6.5 g (63.9%) of (2S,4S)-4-(diphenylphosphino)-2-[(diphenylphosphino)methyl]-1-(p-tolylsulphonyl)-pyrrolidine as a colourless foam. $[\alpha]_D^{20} = -125.8°$ (c=1 in benzene).

The (2S,4R)-1-(p-tolylsulphonyl)-4-[(p-tolylsulphonyl)oxy]-2-pyrrolidinylmethyl p-toluenesulphonate used as the starting material can be prepared as follows:

35.6 g (0.27 mol) of (2S,4R)-4-hydroxyproline were dissolved in 300 ml (0.60 mol) of 2N sodium hydroxide in a 750 ml sulphonation flask which was provided with stirrer, dropping funnel, thermometer and condenser. Thereupon, within 10 minutes there was added dropwise thereto a solution of 63 g (0.33 mol) of p-toluenesulphonyl chloride in 180 ml of diethyl ether. The temperature was held at 16°–20° C. by means of a water bath. After intensive stirring at room temperature for 16 hours, the reaction has finished. The aqueous phase (pH about 7) was separated and back-washed with 250 ml of diethyl ether. The ether phases were back-washed a further twice with 100 ml of deionized water each time. The combined aqueous phases were acidified to pH 2 with 25 ml of concentrated hydrochloric acid (27%) while cooling with ice at 5° C. and stirred for 1.5 hours at 5° C. The separated crystals were filtered off under suction, washed with 1 liter of deionized water and dried for 16 hours in a vacuum drying oven at 40° C./17 mbar. The resulting product (76.2 g of white crystals of melting point 142°–145° C.) was, for purification, dissolved in 200 ml of hot ethanol/water (1:4, v/v) and recrystallized while stirring and slowly cooling to 5° C. The white crystals obtained after drying (73.4 g) were again recrystallized from 150 ml of ethanol/water (1:4, v/v) as previously described and dried in a vacuum drying oven at 50° C./17 mbar. There were obtained 69.4 g (89.6%) of (2S,4R)-4-hydroxy-1-(p-tolylsulphonyl)-2-pyrrolidinecarboxylic acid of melting point 146°–147° C.; $[\alpha]_D^{20} = -87.6°$ (c=1 in ethanol).

57 g (0.20 mol) of (2S,4R)-4-hydroxy-1-(p-tolylsulphonyl)-2-pyrrolidinecarboxylic acid were dissolved in 300 ml of tetrahydrofuran in a 1.5 l sulphonation flask which was provided with a stirrer, thermometer, dropping funnel, condenser with an acetone washing flask connected at the outlet side and argon gasification. 500 ml of 1M diborane solution (tetrahydrofuran; 0.50 mol) were then added dropwise while stirring at 5°–10° C. within 1.2 hours. The reaction mixture was stirred at room temperature overnight. Thereupon, the mixture was decomposed by the slow dropwise addition of 50 ml of deionized water at 0°–5° C. (exothermic reaction) and subsequently evaporated on a rotary evaporator at 50° C./17 mbar. The residue was taken up in 150 ml of deionized water and extracted six times with 300 ml of ethyl acetate each time. The extracts were washed three times with 150 ml of saturated sodium chloride solution each time, dried over sodium sulphate and evaporated on a rotary evaporator at 50° C./17 mbar. For purification, the residue obtained was recrystallized from 100 ml of ethyl acetate. The crystals obtained were filtered off under suction and dried in a drying oven at 40° C./17 mbar. There were thus obtained 34 g (62.7%) of (2S,4R)-4-hydroxy-1-(p-tolylsulphonyl)-2-pyrrolidinemethanol of melting point 133°–134° C.; $[\alpha]_D^{20} = -47.4°$ (c=1 in ethanol).

6.8 g (0.025 mol) of (2S,4R)-4-hydroxy-1-(p-tolylsulphonyl)-2-pyrrolidinemethanol were dissolved in 20 ml of pyridine in a 200 ml sulphonation flask, provided with a stirrer, thermometer, dropping funnel, argon gasification and ice bath, and the solution was cooled to 0° C. Within 45 minutes there was added dropwise at 0°–3° C. while stirring a solution of 12 g (0.063 mol) of p-toluenesulphonyl chloride in 20 ml of pyridine. Pyridine hydrochloride begins to precipitate out after about 1 hour. The mixture was stirred at room temperature overnight and then 100 ml of deionized water were cautiously added dropwise at 0°–10° C. (strong exothermic reaction), a white crystal slurry separating. After stirring in an ice bath for 3 hours, the crystals was filtered off under suction, washed five times with 40 ml of cold deionized water each time and dried for 2 hours in a drying oven at 60° C./17 mbar. For purification, the product obtained was recrystallized from 50 ml of ethyl acetate. The separated crystals were filtered off under suction and dried in a drying oven at 40° C./17 mbar. There were obtained 9.8 g (67.6%) of (2S,4R)-1-(p-tolylsulphonyl)-4-[(p-tolylsulphonyl)oxy]-2-pyrrolidinylmethyl-p-toluenesulphonate of melting point 131°–134° C.; $[\alpha]_D^{20} = -77.2°$ (c=1 in benzene).

EXAMPLE 3

50 g (0.39 mol) of dihydro-4,4-dimethyl-2,3-furandione and 300 ml of toluene were placed in a 1 liter stirring steel autoclave. In order to remove the air from the system, the autoclave was evacuated five times with a high vacuum pump and in each case gassed with 10 bar of hydrogen. The autoclave, heated to 40° C., was thereupon again evacuated. Then, the yellow catalyst solution, prepared from 0.029 g (0.063 mmol) of chloronorbornadiene-rhodium (I) dimer and 0.082 g (0.126 mmol) of (2S,4S)-4-(diphenylphosphino)-2-[(diphenylphosphino)methyl]-1-(diphenylphosphinyl)pyrrolidine in 50 ml of toluene, was introduced and then the autoclave was gassed with 40 bar of hydrogen. The hydrogenation was carried out with intensive stirring at 40° C. and a constant hydrogen pressure of 40 bar and was finished after 20 hours. The pale yellow solution was then rinsed from the autoclave with toluene and the solvent was removed by evaporation on a rotary evaporator at 60° C./17 mbar. The residue (54.7 g) was distilled at 130°–150° C. (bath temperature) and 0.05 mbar. There was obtained 50.2 g (98.9%) of crude R-(α-hydroxy-β,β-dimethyl-γ-butyrolactone) with an optical purity of 84.3%; $[\alpha]_D^{20} = -43.1°$ (c=1 in water).

EXAMPLE 4

50 g (0.39 mol) of dihydro-4,4-dimethyl-2,3-furandione and 300 ml of ethyl acetate were placed in a 1 liter stirring steel autoclave. In order to remove the air from the system, the autoclave was evacuated five times with a high vacuum pump and in each case gassed with 10 bar of hydrogen. The autoclave, heated to 40° C., was thereupon again evacuated. Then, the yellow catalyst solution, prepared from 0.029 g (0.063 mmol) of chloronorbornadiene-rhodium (I) dimer and 0.076 g (0.126 mmol) of (2S,4S)-4-(diphenylphosphino)-2-[(diphenylphosphino)methyl]-1-(p-tolylsulphonyl)-pyrrolidine in 50 ml of ethyl acetate, was introduced and then the autoclave was gassed with 40 bar of hydrogen. The hydrogenation was carried out with intensive stirring at 60° C. and a constant hydrogen pressure of 40 bar and was finished after 8 hours. The pale yellow solution was then rinsed from the autoclave with ethyl acetate and the solvent was removed by evaporation on a rotary evaporator at 60° C./17 mbar. The residue (59.9 g) was distilled at 130°–150° C. (bath temperature) and 0.05 mbar. There were obtained 50.6 g (99.8%) of crude R-(α-hydroxy-β,β-dimethyl-γ-butyrolactone) with an optical purity of 81.8%; $[\alpha]_D^{20} = -41.7°$ (c=1 in water).

We claim:

1. Chiral phosphines of the formula

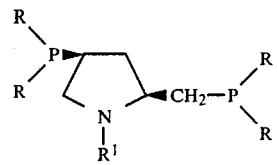

wherein R represents aryl and $R^1$ represents a group of the formula

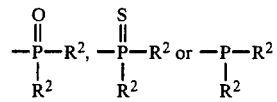

in which $R^2$ represents aryl, di(lower alkyl)amino, hydroxy, aryloxy or lower alkoxy.

2. The phosphines of claim 1 wherein $R^1$ represents a group of the formula

3. The phosphines of claim 2 wherein R represents phenyl, p-tolyl or m-tolyl and $R^2$ in the group $R^1$ represents phenyl, p-tolyl or m-tolyl.

4. The phosphine of claim 3 which is (2S,4S)-4-diphenylphosphino-2-[(diphenylphosphino)methyl]-1-(diphenylphosphinyl)-pyrrolidine.

5. The phosphine of claim 3 which is (2S,4S)-4-(di-p-tolylphosphino)-2-[(di-p-tolylphosphino)methyl]-1-diphenylphosphinyl)-pyrrolidine.

6. The phosphine of claim 3 which is (2S,4S)-4-di-m-tolylphosphino)-2-[(di-m-tolylphosphino)methyl]-1-(diphenylphosphinyl)-pyrrolidine.

7. The phosphine of claim 3 which is (2S,4S)-4-(diphenylphosphino)-2-[(diphenylphosphino)methyl]-1-(di-p-tolylphosphinyl)-pyrrolidine.

8. The phosphine of claim 3 which is (2S,4S)-4-(diphenylphosphino)-2-[(diphenylphosphino)methyl]-1-(di-m-tolylphosphinyl)-pyrrolidine.

* * * * *